United States Patent [19]

Pelmulder

[11] Patent Number: 5,609,771

[45] Date of Patent: Mar. 11, 1997

[54] METHOD OF SEPARATING RED BLOOD CELLS FROM A VOLUME OF BLOOD

[75] Inventor: John P. Pelmulder, Chatsworth, Calif.

[73] Assignee: International Remote Imaging Systems, Inc., Chatsworth, Calif.

[21] Appl. No.: 398,432

[22] Filed: Mar. 3, 1995

[51] Int. Cl.$^6$ ................................................. B01D 21/00
[52] U.S. Cl. ................................................. 210/800; 210/767
[58] Field of Search ................................. 210/767, 800, 210/801, 749, 513; 530/412, 417

[56] References Cited

U.S. PATENT DOCUMENTS

| | | | |
|---|---|---|---|
| 4,181,609 | 1/1980 | Wardlaw et al. . | |
| 4,255,256 | 3/1981 | Ferrante et al. | 210/730 |
| 4,436,634 | 3/1984 | Wells | 210/800 |
| 4,663,058 | 5/1987 | Wells et al. | 210/801 |
| 4,765,899 | 8/1988 | Wells et al. | 210/519 |
| 4,968,432 | 11/1990 | Antwiler | 210/677 |
| 5,118,428 | 6/1992 | Sand et al. | 210/749 |
| 5,282,982 | 2/1994 | Wells | 210/800 |

OTHER PUBLICATIONS

John R. Wells, Department of Medicine, Sorvail Applications Brief, No. 21, Dec., 1983, *Cell Separation at Unit Gravity Using CELSEP*, DuPont Company, Wilmington, Delaware, USA.

*Primary Examiner*—John Kim
*Attorney, Agent, or Firm*—Limbach & Limbach L.L.P.

[57] ABSTRACT

A method of separating red blood cells within a volume of blood provides rapid separation of the red blood cells to permit efficient analysis of the white blood cells. First, a container is filled with the volume of blood while the container is in a substantially vertical position. The container has an open top portion, a side wall, and a closed bottom portion. The volume of blood in the container defines a first surface region having a particular spatial relationship to the side wall. Then, the container is moved to a first position, away from the substantially vertical position. The container is maintained at the first position for at least a first predetermined time such that red blood cells within the volume of blood settle substantially to the side wall of the container. The cross sectional area of the container at the first surface region of the volume of blood is such that the particular spatial relationship is maintained between the first surface region and the side wall. Then, the container is moved to a second position substantially without agitating the volume of blood contained therein (the second position is closer to the substantially vertical position than is the first position) and the container is maintained at the second position for at least a second predetermined time so that the red blood cells settled substantially to the side wall of the container slide to the closed bottom portion of the container.

17 Claims, 2 Drawing Sheets

5,609,771

METHOD OF SEPARATING RED BLOOD CELLS FROM A VOLUME OF BLOOD

TECHNICAL FIELD OF THE INVENTION

The present invention relates to a method of separating red blood cells from a volume of blood, and more particularly, to a method of separation using a container to settle the red blood cells rapidly.

BACKGROUND OF THE INVENTION

White blood cell analysis is an important tool in the diagnosis of many diseases and disorders in humans. However, there are approximately 1000 times more red cells than white cells in human blood, and the presence of the red cells interfere with analysis of the white cells. Thus, there is a need to remove the red cells quickly to permit efficient analysis of the white cells.

SUMMARY OF THE INVENTION

The present invention is a method of separating a substantial amount of red blood cells from a volume of blood. With most of the red blood cells separated from the volume of blood, the remaining white blood cells can be efficiently analyzed.

The method comprises filling a portion of the length of a small cross-sectional area container with a volume of blood. An initial settling process is carried out with the container non-vertical, in order to decrease the distance that the red blood cells in the volume of blood must travel to settle to the container wall. The cross-sectional area, shape, and material of the container are such that surface tension maintains a particular spatial relationship and location of the surface region of the volume of blood to the container wall, independent of the orientation of the container. The blood thus will not run out of the container, even if the container is horizontal. After at least a first predetermined amount of time, such that a large number of red blood cells have settled from the volume of blood to the container wall, the container is moved to be closer to vertical, thus causing the settled red blood cells to move along the container wall toward the bottom of the volume of blood in the container without remixing the settled red cells with the plasma and white cells. Preferably, after at least a second predetermined period of time, the container is then moved to a substantially vertical position, without agitating the volume of blood contained therein, so that the separation of the red cells from the plasma and white cells is maintained. In the vertical orientation, the area of the interface between the settled red cells and the white cells and plasma is minimized. The removal of the plasma containing white cells, for further treatment or analysis, can thus be carried out with minimal entrainment of the settled red cells.

BRIEF DESCRIPTION OF THE FIGURES

FIG. 1 shows a single container, which may be one of a plurality of such containers, containing a volume of blood. The container of FIG. 1 is in a substantially vertical position.

DETAILED DESCRIPTION OF THE INVENTION

Figure 1:
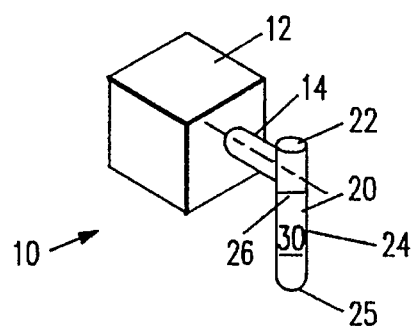
FIG. 1 is an illustration of a blood cell separation apparatus which may perform the method of the present invention.

Referring to FIG. 1 there is shown an apparatus 10 suitable to carry out the present invention method of separating a substantial number of red blood cells from a volume of blood even if the blood constituents are uniformly dispersed throughout the volume of blood. The apparatus 10 comprises a rotary actuator 12 having a shaft 14 oriented horizontally. Attached to the end of shaft 14 is a container 20. The container 20 is characterized by having an open portion 22, a side wall 24, and a bottom closed portion 25.

Figure 3:
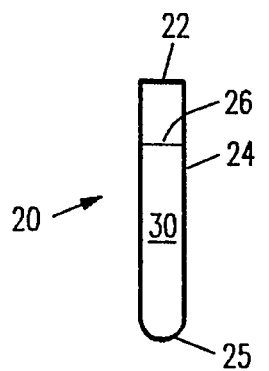
FIG. 3 is an illustration of the container of FIG. 1, in a substantially vertical position immediately after the container has been filled with a volume of blood.

In accordance with the present invention, initially, a volume of blood 30 is placed in the container 20, preferably while the container 20 is in an upright position. However, the volume of blood 30 may also be onto the container 20 while the container 20 is away from the vertical position. After the volume of blood 30 is placed into the container 20, the surface region 26 of the volume of the blood has a particular relationship to the side wall 24 of the tube 20. For example, in FIGS. 1 and 3, the surface region 26 is shown as being substantially perpendicular to the side wall 24 of the container 20.

Figure 2:
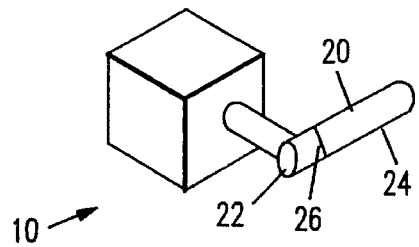
FIG. 2 is an illustration of the blood cell separation apparatus of FIG. 1, the container having been rotated to a substantially horizontal position.
Figure 4:
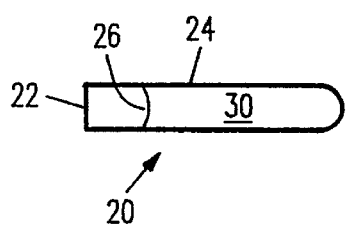
FIG. 4 is an illustration of the container of FIG. 3, in a substantially non-vertical position after the container has been filled with a volume of blood but before passage of a first predetermined amount of time such that substantial settling of red cells has not yet occurred.

The container 20 is next moved to a position away from the upright position, as shown in FIGS. 2 and 4 to enhance the settling time of the red blood cells from the volume of blood. That is, by moving the container away from the upright position, the distance that the red blood cells in the volume of blood 30 must travel to settle at the wall 24 of the container 20 is reduced. For example, referring to FIG. 4, if the container 20 is a cylindrical tube and the tube is moved to a substantially horizontal position, the maximum distance that the red blood cells must travel to settle at the wall 24 of the tube is merely the diameter D of the tube, rather than the entire length L of the volume of blood 30 in the tube. Since the settling velocity is the same in either case, the settling time of the red blood cells when the tube is in the substantially horizontal configuration is reduced by the ratio D/L from the settling time of the red blood cells when the container 20 is in the upright position. In addition, chemical settling enhancers, as disclosed, for example, in copending application Ser. No. 08/052,504 (Composition and Method for Enrichment of White Blood Cells from Whole Human Blood, Kass et al., filed Apr. 26, 1993, and assigned to the assignee of the present invention) may be employed to further reduce the settling time.

Furthermore, the cross-sectional area, shape, and material of the container 20 are such that surface tension maintains the particular relationship of the surface region 26 of the volume of blood 30 to the wall 24 of the container 20 even when the container is not vertical. For example, it has been found that surface tension maintains the particular relationship in a cylindrical glass tube having an inside diameter of 4.7 millimeters (mm) (i.e. a cross-sectional area of approximately 69.4 $mm^2$). Materials other than glass, so long as blood is non-wetting to the material, may be employed. For example, the container may be made of a plastic material such as polypropylene.

Finally, the walls of the container must be rounded, with no sharp corners. If the walls of the container had sharp corners, capillary attraction would tend to draw the surface region of the volume of blood along the wall of the container. If such a container were positioned horizontally, the capillary attraction would be unimpeded by gravity and would thus spread red blood cells into areas which should be kept clean, perhaps even causing blood to spill out the end of the container.

FIG. 4 shows the container 20 in a horizontal position, with the various types of cells and other constituents of the blood and chemical settling enhancers (if used) uniformly dispersed throughout the volume of blood.

Figure 5:
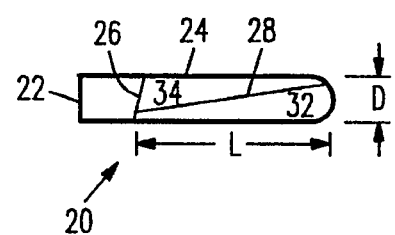
FIG. 5 is an illustration of the container of FIG. 4 after the container has been in the substantially horizontal position for at least the first predetermined amount of time such that substantial settling of red blood cells has occurred.

FIG. 5 shows the container 20 in the horizontal position after the container 20 has been in the horizontal position for at least a first predetermined period of time, the first predetermined period of time being such that a substantial amount of settling of the red cells in the volume of blood can occur. The settled red blood cells are shown in region 32. The white blood cells and other plasma constituents are shown in region 34. Region 28, separating the region of settled red cells 32 from the region of other constituents 34, is horizontal (i.e. perpendicular to the gravitational direction). However, surface region 26 separating the liquid from the air is still substantially perpendicular to the container wall 24 and at the same location along the length of the wall because of the effects of surface tension, and despite gravity.

Figure 6:
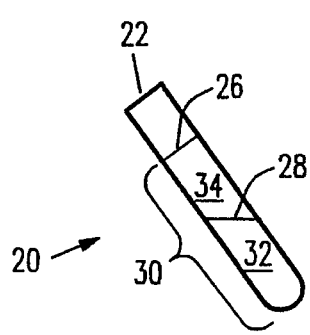
FIG. 6 is an illustration of the container of FIG. 5 after the at least first predetermined amount of time and after the container has been moved from the substantially horizontal position to a position between horizontal and vertical.

Next, after the at least first predetermined time, the container 20 is moved to a position between horizontal and vertical. FIG. 6 is an illustration of the container 20 and the volume of blood after having been moved to such a position. After being moved to this position from the horizontal position, the settled red cells 32 move down the container wall 24 toward the bottom of container 20, displacing the plasma 34 upward toward the end region 22 of the container 20. The velocity of this relative motion is preferably limited such that remixing of the settled red cells into the plasma is minimized. Depending on the settling enhancers used, the angle of inclination may need to be limited and the time of tilt extended to accomplish this counter flow movement of the two types of cells without remixing. Furthermore, it has been found that if the length of blood region, L, is substantially greater than about 10 times the container diameter, D, the time required to move the red cells to the bottom of the container, without remixing, becomes excessive.

Figure 7:
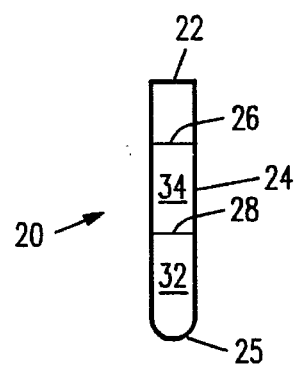
FIG. 7 is an illustration of the container of FIG. 6, after an at least second predetermined amount of time and after the container has been moved to a vertical position for removal of the plasma/white cell portion of the volume of blood.

At this point, the plasma/white cell portion 34 of the volume of blood 30 may be removed. However, in a preferred embodiment of the present invention, after substantially all of the settled red cells have moved to the bottom of the container, the container is then moved to the vertical position. FIG. 7 is an illustration of the container after it has been moved to the vertical position. In this position, the area of interface 28 between the red blood cells in region 32 and the other blood constituents in region 34 is minimized, thus facilitating removal of the plasma/white cell portion 34 without disturbing or mixing the red cell region 32.

Alternatively, the container can be moved from the substantially horizontal position (FIG. 5) to the vertical position (FIG. 7) in a continuous move, if the rate of movement is very slow.

In a further alternate embodiment of the present invention, rather than the container 20 being moved to a substantially horizontal position after it is filled with the volume of blood 30, the container 20 is instead moved to a position away from vertical, other than substantially horizontal. Thus, not only is the settling time of the red blood cells to the container wall 24 decreased (although the settling time is not decreased as much as if the container 20 were substantially horizontal), but also, red cells that settle to the container wall 24 then travel down the container wall 24 to the bottom of the container 25 without having to reorient the container 20.

In a further alternate embodiment of the present invention, the container 20 is fixed at an inclined angle between vertical and horizontal, and the container 20 is filled and settling occurs with the container at this inclined angle. Thus, red cells that settle to the container wall 24 travel down the wall 24 without reorienting the container 24. At the completion of settling, the plasma and red blood cells are removed with the container 20 still at the same angle. Preferably, the angle of inclination is large enough such that the red blood cells travel down the container wall 24 without significant sticking. As with the previously described alternate embodiment, the settling time is not as short as if the tube were horizontal, but the settling time will still be substantially shorter than if the tube were vertical.

Figure 8:
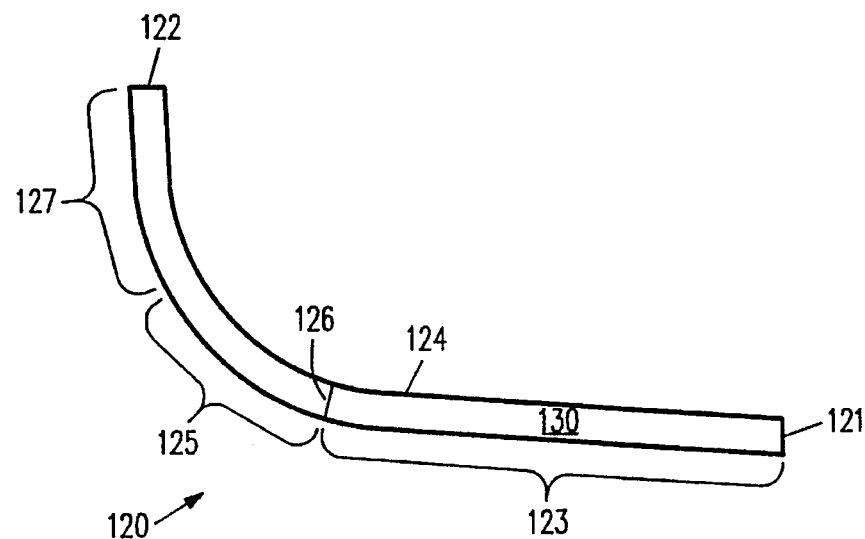
FIG. 8 is an illustration of another container which may used in performing the method of the present invention. The container is a curved inclined tube in which blood and its constituent parts are moved along the tube in practicing the method of the present invention.

Referring now to FIG. 8, there is shown another container 120 suitable to carry out the method of the present invention. The container 120 is a tube having an entrance end 121 and an exit end 122. The tube 120 has a substantially straight region 123 at the entrance end 121 and for a short distance therefrom. The tube 120 has a curved region 125 near its middle and another straight region 127 at its exit end 122. The volume of blood 130 from which red cells are to be separated is loaded into the container 120 through the entrance end 121 where the region 123 is substantially straight, filling the straight horizontal region 123. As discussed above with respect to FIGS. 4 and 5, the maximum settling distance for the red cells, and thus the settling time, is reduced in this configuration.

Figure 9:
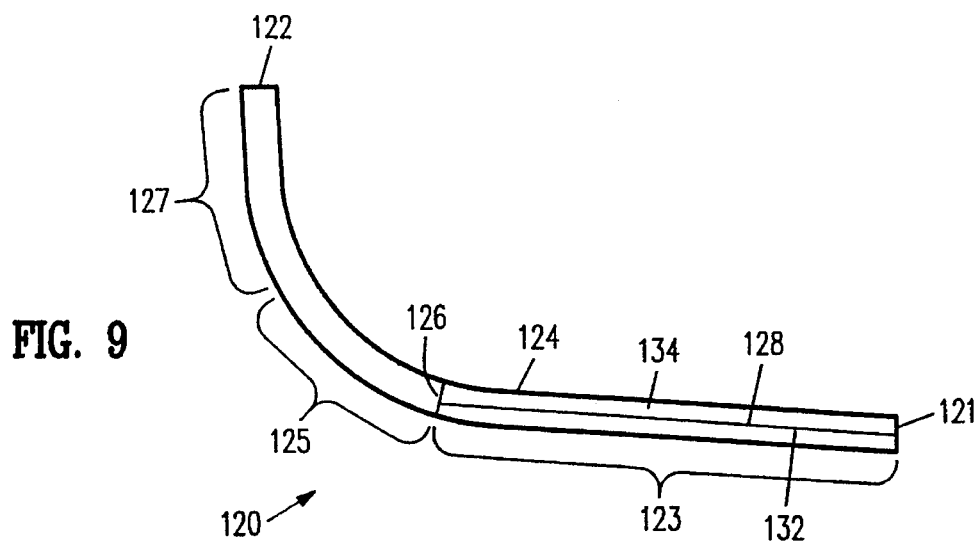
FIG. 9 is an illustration of the container of FIG. 8, showing the red cells of the volume of blood settled in a region at the bottom of the tube, with the plasma and white cells above.
Figure 10:
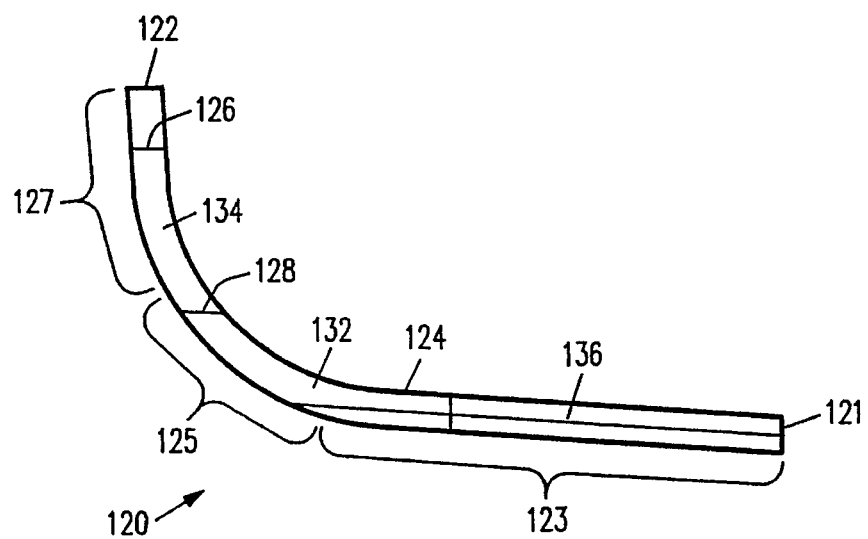
FIG. 10 is an illustration of the container of FIG. 8, showing the volume of blood displaced farther along the tube than in FIG. 9, into the vertical region.

After at least a predetermined amount of time, such that the red cells of the volume of blood are settled in a region 132 at the bottom of the tube, with the plasma and white cells above (FIG. 9), the volume of blood is displaced along tube 120 into the inclined region 125. This may be done, for example, by pumping saline solution into the container 120, as shown in FIG. 10 (the saline solution is denoted by numeral 136). As with the embodiment of the present invention illustrated by FIGS. 3–7, there is a relative counterflow motion of the white cells and the red cells along the axis of the tube in the inclined region, and the velocity of the displacement of the volume of blood along the tube 120 is preferably limited such that remixing of the settled red cells into the plasma is minimized.

However, in contrast to the embodiment of the present invention illustrated by FIGS. 3–7, the angle of inclination of the container 120 in region 125 does not need to be steep enough to cause red blood cells to travel down the container wall 124 since it is the plasma and white blood cells that are being moved. A major advantage to the FIG. 8 embodiment is that the plasma and white blood cells are displaced into a region of the container 120 which has not previously contained whole blood and red blood cells. Thus, the amount of residual red blood cells in the plasma is minimized.

Finally, as shown in FIG. 10, the volume of blood 130 is displaced farther along the tube into the vertical region 127 where final separation takes place. At the end of the settling, the blood is forced out of the exit end 122. However, the blood which entered the tube 120 with its constituents uniformly dispersed, now exits with the plasma and white blood cells leaving first followed by the settled red blood cells and the driving saline solution.

The method of the present invention is the unique beneficial result of combining the geometry of a flow tube settler, which is well known in the process industry, with air bubble separation of moving fluids in capillary tubes, which is well known in the chemistry analyzer industry, in a stationary or intermittently flowing tube. The resulting technique provides fast settling of very small volumes of blood in a configuration that permits harvesting white cells with minimal contamination by the settled red cells.

Another advantage of the present invention is that, while the plasma may stratify into layers of various white blood cell types during the horizontal settling period, this stratification is overcome by the change to an inclined or vertical orientation. Additional stratification that may occur while the container 20 is angled or vertical is negligible. As a result, analytes are substantially uniformly distributed throughout the plasma, which makes it easier to harvest a representative aliquot of the white blood cells for analysis.

What is claimed is:

1. A method of separating red blood cells within a volume of blood, the method comprising:

a) filling a container with the volume of blood while the container is in a substantially vertical position, the container having an open top portion, a side wall, and a closed bottom portion, the volume of blood in the container defining a first surface region having a particular spatial relationship to the side wall;

b) moving the container to a first position, away from the substantially vertical position, and maintaining the container at the first position for at least a first predetermined time such that red blood cells within the volume of blood settle substantially to the side wall of the container, the cross sectional area of the container at the first surface region of the volume of blood being such that the particular spatial relationship is maintained between the first surface region and the side wall even when the container is moved to the first position; and c) moving the container to a second position substantially without agitating the volume of blood contained therein, the second position being closer to the substantially vertical position than is the first position, and maintaining the container at the second position for at least a second predetermined time, whereby the red blood cells settled substantially to the side wall of the container in step b) slide to the closed bottom portion of the container.

2. The method of claim 1, wherein step b) causes a second surface region to form between a plasma portion and a red blood cell portion within the volume of blood, and the second surface region has a spatial relationship to the side wall different from the particular spatial relationship of the first surface region to the side wall.

3. The method of claim 2, further comprising:

d) after step c), removing at least some of the plasma portion of the volume of blood.

4. The method of claim 3, wherein the second position is the substantially vertical position.

5. The method of claim 4, wherein the first position is the substantially horizontal position.

6. The method of claim 1, wherein the second position is a substantially vertical position.

7. The method of claim 1, wherein the second position is a position between the substantially horizontal position and the substantially vertical position, the method further comprising:

d) after step c), moving the container to the vertical position substantially without agitating the volume of blood.

8. The method of claim 7, wherein step b) causes a second surface region to form between a plasma portion and a red blood cell portion within the volume of blood, and the second surface region has a spatial relationship to the side wall different from the particular spatial relationship of the first surface region to the wall, the method further comprising:

e) after step d), removing at least some of the plasma portion of the volume of blood.

9. A method of separating red blood cells within a volume of blood, the method comprising:

a) filling a container with the volume of blood while the container is in a first position, away from a substantially vertical position, the container having an open top portion, a side wall, and a closed bottom portion, the volume of blood in the container defining a first surface region, the first surface region of the volume of blood having a particular spatial relationship to the side wall;

b) moving the container to a second position, different from the first position;

(c) maintaining the container at the second position for at least a first predetermined time such that red blood cells within the volume of blood settle substantially to the side wall of the container, a cross-sectional area of the container at the first surface region being such that the particular spatial relationship of the first surface region to the side wall is maintained even though the second position is different from the first position.

10. The method of claim 9, wherein the second position is a substantially horizontal position, the method further comprising:

d) moving the container to a third position, substantially without agitating the volume of blood contained therein, the third position being closer to the substantially vertical position than is the second position, and maintaining the container at the third position for at least a second predetermined time, whereby the red blood cells settled substantially to the side wall of the container in step b) slide to the closed bottom portion of the container.

11. The method of claim 10, wherein step c) causes a second surface region to form between a plasma portion and a red blood cell portion within the volume of blood, and the second surface region has a spatial relationship to the side wall different from the particular spatial relationship of the first surface region to the side wall.

12. The method of claim 11, further comprising:
   e) after step d), removing at least some of the plasma portion of the volume of blood.

13. The method of claim 9, wherein step c) causes a second surface region to form between a plasma portion and a red blood cell portion within the volume of blood, and the second surface region has a spatial relationship to the side wall different than the particular spatial relationship of the first surface region to the side wall.

14. The method of claim 13, further comprising:
   d) after step c), removing at least some of the plasma portion of the volume of blood.

15. A method of separating red blood cells within a volume of blood, the method comprising:
   a) filling a container with the volume of blood, the container being defined by a side wall, the container having a substantially horizontal entrance portion through which the container is filled with the volume of blood and an inclined portion, a first end of the inclined portion being adjacent the entrance portion the volume of blood in the container defining a first surface region having a particular spatial relationship to the side wall of the entrance portion;
   b) waiting at least a first predetermined amount of time such that red blood cells within the volume of blood settle substantially to the side wall of the container;
   c) displacing the volume of blood into the inclined portion of the container substantially without agitating the volume of blood and without moving the container, and maintaining the volume of blood in the inclined portion of the container for at least a second predetermined amount of time, whereby the red blood cells settled substantially to the side wall of the container in step b) slide to a bottom region of the volume of blood.

16. The method of claim 15, wherein step b) causes a second surface region to form between a plasma portion and a red blood cell portion within the volume of blood, the method further comprising:
   d) after step c), removing at least some of the plasma portion of the volume of blood.

17. The method of claim 15, wherein the container further has a substantially vertical portion adjacent a second end of the inclined portion, and wherein step b) causes a surface region to form between a plasma portion and a red blood cell portion within the volume of blood, the method further comprising:
   d) displacing the volume of blood into the substantially vertical portion of the container substantially without agitating the volume of blood; and
   e) removing at least some of the plasma portion of the volume of blood.

* * * * *